United States Patent [19]
Yoshioka et al.

[11] Patent Number: 4,958,040
[45] Date of Patent: Sep. 18, 1990

[54] PROCESS FOR THE PREPARATION OF DIORGANOHALOGENOSILANES

[75] Inventors: Hiroshi Yoshioka, Tokyo; Masaaki Yamaya, Annaka; Hiromi Ohsaki; Akira Hayashida, both of Joetsu, all of Japan

[73] Assignee: Shin-Etsu Chemical

[21] Appl. No.: 410,202

[22] Filed: Sep. 21, 1989

[30] Foreign Application Priority Data

Sep. 28, 1988 [JP] Japan ................... 63-243685

[51] Int. Cl.$^5$ ............................... C07F 7/08
[52] U.S. Cl. ................... 556/467; 556/468
[58] Field of Search ................... 556/467, 468

[56] References Cited

U.S. PATENT DOCUMENTS

| 3,432,537 | 3/1969 | Guinet et al. ........................ 556/468 |
| 3,639,105 | 2/1972 | Atwell et al. ................... 556/468 X |
| 4,059,608 | 11/1977 | Coles et al. ........................ 556/468 |
| 4,079,071 | 3/1978 | Neale ........................ 556/468 |
| 4,363,925 | 12/1982 | Acker ................... 556/468 X |

FOREIGN PATENT DOCUMENTS

| 47-13314 | 7/1972 | Japan ........................ 556/467 |
| 49-93324 | 9/1974 | Japan ........................ 556/467 |
| 52-31854 | 8/1977 | Japan ........................ 556/467 |
| 52-151130 | 12/1977 | Japan ........................ 556/467 |
| 57-176911 | 10/1982 | Japan ........................ 556/467 |
| 62-81390 | 4/1987 | Japan ........................ 556/467 |
| 53-95922 | 8/1987 | Japan ........................ 556/467 |

Primary Examiner—Paul F. Shaver

[57] ABSTRACT

A process for preparing diorganohalogenosilanes wherein diorganodihalogenosilanes are reacted with at least one organosilicon compound having at least one ≡Si—H bond in the molecule and selected from polysilanes, polycarbosilanes and polysilphenylenes is described. This reaction proceeds in the presence of a Lewis acid.

17 Claims, 1 Drawing Sheet

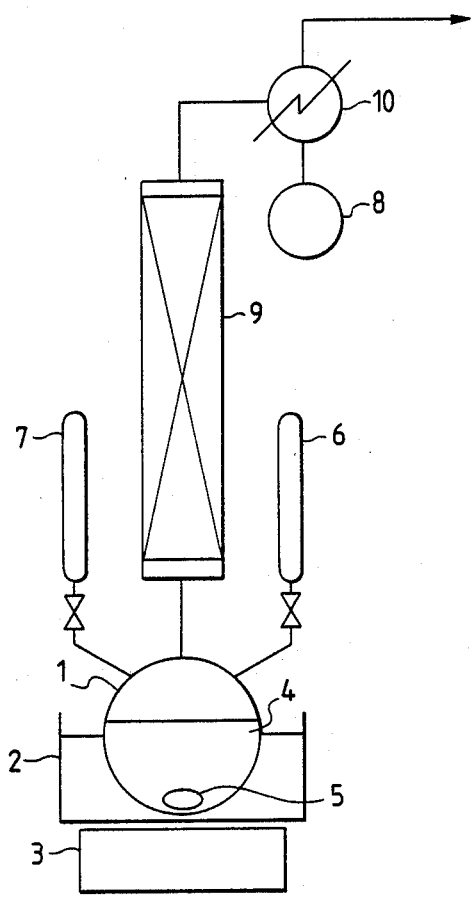

PROCESS FOR THE PREPARATION OF DIORGANOHALOGENOSILANES

BACKGROUND OF THE INVENTION

1. Field of the Invention

This invention relates to a process for preparing diorganohalogenosilanes. The diorganohalogenosilanes are important compounds in the industry of organosilicon compounds for use as starting materials for imparting reactivity to various types of organopolysiloxanes.

2. Description of the Prior Art

Organohalogenosilanes have been heretofore prepared by the following several processes.

(1) Process wherein silicon powder and alkyl halides or aryl halides are reacted in the presence of a copper catalyst by a so-called direct method, thereby obtaining the diorganohalogenosilanes along with diorganodihalogenosilanes.

(2) Process wherein two types of silicon compounds are subjected to redistribution reaction using amines or Lewis acids to collect the resultant diorganohalogenosilane as set forth in Japanese Laid-open Patent Application Nos. 47-13,314, 49-93,324 and 62-81,390.

(3) Process wherein the Si-Cl bond of chlorosilanes is reduced into a $\equiv$SiH bond as described in Japanese Laid-open Patent Application Nos. 52-151,130 and 53-95,922.

The process (1) has now been used on an industrial scale in order to mainly produce diorganodihalogenosilanes. However, even when the type of catalyst and reaction conditions are changed, the production rate of diorganohalogenosilanes is extremely low. Thus, this process is not suitable for the production of diorganohalogenosilanes.

The process (2) fundamentally requires high temperature and high pressure conditions. Accordingly, it involves complicated side reactions through exchange reactions of $\equiv$Si—CH$_3$, $\equiv$Si—H and $\equiv$Si—Cl, so that the production rate of diorganohalogenosilane is low with an attendant disadvantage that isolation of the diorganohalogenosilane is difficult.

The process (3) makes use of reducing agents which are expensive. In addition, during the reduction of diorganodihalogenosilanes, two chlorine atoms are all reduced with the result that the reaction proceeds to an extent of diorganodihydrosilane. It is difficult to selectively stop the reaction at the stage where diorganohalogenosilanes are produced.

To overcome the disadvantages involved in the process (2), there have been proposed improved processes of preparing diorganohalogenosilanes.

In one such improvement, Japanese Patent Publication No. 52-31,854 proposed a process wherein methylhydrogenpolysiloxane and a diorganodichlorosilane are reacted in the presence of a catalyst, thereby causing an exchange reaction with the hydrogen atom bonded to the silicon atom of the methylhydrogenpolysiloxane. However, this improved process is disadvantageous in that the catalyst and starting materials are expensive and that the yield of a dimethylmonochlorosilane product is low.

Japanese Laid-open Patent Application No. 57-176,911 proposes a process wherein dimethylsilane and dimethyldichlorosilane are subjected to disproportionation reaction similarly to the above process. However, the starting dimethylsilane is expensive. Since dimethylsilane has a boiling point of $-20°$ C. and is gaseous at room temperature, so that it is dangerous and handling of this silane is industrially difficult.

SUMMARY OF THE INVENTION

It is accordingly an object of the invention to provide a process for preparing diorganohalogenosilanes inexpensively on an industrial scale.

It is another object of the invention to provide a process for selectively preparing organohalogenosilanes in high yield.

The above objects can be achieved, according to the invention, by a process which comprises reacting a diorganodihalogenosilane and at least one organosilicon compound having at least one $\equiv$Si—H bond in the molecule and selected from polysilanes, polycarbosilanes and polysilphenylenes in the presence of a Lewis acid. This process may be carried out by a batch-wise manner or continuously.

BRIEF DESCRIPTION OF THE DRAWING

The sole FIGURE is a schematic view of an apparatus for carrying out the process of the invention.

DETAILED DESCRIPTION AND EMBODIMENTS OF THE INVENTION

The polysilanes, polycarbosilanes and polysilphenylenes having at least one $\equiv$Si—H bond in the molecule are used as one of the starting materials in the process of the invention and are generically represented by the following formula

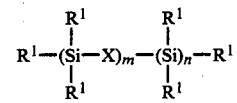

wherein each $R^1$ independently represents a hydrogen atom, a lower alkyl group having from 1 to 3 carbon atoms, an alkenyl group, or an aryl group provided that at least one $R^1$ is a hydrogen atom, X represents —(CH$_2$)$_l$— wherein l is an integer of from 1 to 3, or

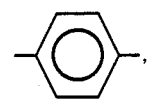

m is an integer of from 0 to 3 and n is an integer of from 1 to 5 provided that $m+n \geq 2$.

Examples of the alkenyl group represented by $R^1$ include a vinyl group, an allyl group and the like, and examples of the aryl group include a phenyl group, tolyl group, a xylyl group and the like.

Specific examples of the organosilicon compounds include H(SiMe$_2$)$_2$H, H(SiMe$_2$)$_3$H, H(SiMe$_2$)$_4$H, H(SiMe$_2$)$_5$H, HSiMe$_2$—CH$_2$—SiMe$_2$H, HSiMe$_2$—CH$_2$—SiMeH$_2$, H$_2$SiMe—CH$_2$—SiMeH$_2$, HSiMe$_2$—CH$_2$—(SiMe$_2$)$_2$H, H(SiMe$_2$—CH$_2$)$_2$—SiMe$_2$H, H$_2$SiMe—CH$_2$—(SiMe$_2$—CH$_2$)$_2$—SiMe$_2$H, H(SiMe$_2$—CH$_2$)$_3$—(SiMe$_2$)$_2$H, H(SiMe$_2$—CH$_2$)$_2$—SiMe$_2$—SiMeH$_2$, H$_2$—SiMeH—SiMeH$_2$, H(SiMe$_2$—CH$_2$)$_2$—SiMe$_2$—SiMe$_2$H, HSiMe$_2$—CH$_2$CH$_2$—SiMe$_2$—(CH$_2$)$_3$—SiMe$_2$—SiMe$_2$H, and

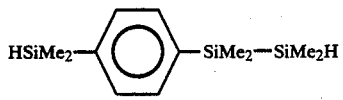

wherein Me represents CH₃—. Of these, H(SiMe₂)₂H, HSiMe₂—CH₂—SiMeH₂ and HSiMe₂—CH₂—SiMe₂H are preferred. Also, H(SiMe₂)₃H is also preferred.

The diorganodihalogenosilane used as the other ingredient is of the following general formula

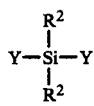

wherein each $R^2$ independently represents an alkyl group having from 1 to 10 carbon atoms, an alkenyl group or an aryl group and each Y independently represents chlorine, bromine or iodine. The alkenyl and aryl groups are the same as those indicated in the foregoing formula. Specific examples of the diorganodihalogenosilane include Me₂SiCl₂, Me₂SiBr₂, Et₂SiCl₂, MePrSiCl₂, (C₆H₁₃)MeSiCl₂, (C₆H₁₁)MeSiCl₂, (CH₂=CH)MeSiCl₂, C₆H₅MeSiCl₂ and the like, in which Me represents a methyl group and Pr represents a propyl group. Of these, Me₂SiCl₂ is preferred because it is mass-produced and is thus inexpensive. This permits a Me₂HSiCl compound to be obtained inexpensively from Me₂SiCl₂ according to the process of the invention, which has a great merit in the organosilicon industry.

The Lewis acid used as the catalyst includes, for example, AlCl₃, FeCl₃, SnCl₄ and the like, of which AlCl₃ is preferred because of the high reaction velocity. The amount of the Lewis acid is in amounts not less than 0.1 wt % of the total of the reaction system.

According to one embodiment of the invention, a diorganodihalogenosilane is charged into a reactor and, after addition of a Lewis acid, at least one organosilicon compound defined before is added to or dropped into the mixture, whereupon a diorganohalogenosilane is produced. In this embodiment, the reaction is usually carried out at a temperature ranging from room temperature to the refluxing temperature of the diorganodihalogenosilane. Because the resultant diorganohalogenosilane is apt to undergo further disproportionation reaction if present in the liquid phase containing the catalyst, it is usual to add a terminator for the reaction to the reaction system when a desired yield of the diorganohalogenosilane is attained. The timing of the addition should be experimentally confirmed.

Examples of such a terminator includes amines such as pyridine, tributylamine and the like, and siloxanes such as dimethylsilicone oil, methylphenylsilicone oil and the like. The thus produced diorganohalogenosilane can be readily isolated from the reaction system by any known distillation or fractionating technique. The above process is a batch-wise procedure, by which a yield of from 60 to 85% is attained.

In accordance with another embodiment of the invention, the reaction of the invention may be carried out in the following manner wherein the reaction system is maintained at high temperatures which cause a diorganohalogensilane product to be removed from the reaction system. This procedure may be effected by a batch-wise manner or continuously.

In this procedure, the starting materials are charged into a reactor similar to the first embodiment, but the reaction system should be kept at a temperature not lower than the boiling point of the diorganohalogenosilane product in order to cause the product not to be left in the liquid phase of the reaction system over a long term. This is because, as stated above, the diorganohalogenosilane product is very liable to undergo further disproportionation reaction in the liquid phase containing the catalyst, thus leading to a lowering of yield. To avoid this, once produced diorganohalogenosilane should be removed or expelled from the reaction system as soon as possible, preferably simultaneously with the formation. For this purpose, it is preferred to distil off the diorganohalogenosilane along with the starting diorganodihalogenosilane from the reaction system.

The concentration of the diorganohalogenosilane in the distillate should be as high as possible from the economical standpoint. However, the upper limit should preferably be 70 mole %. Over 70 mole %, the yield of the diorganohalogenosilane starts to lower.

When the reaction system is under distillation, the diorganohalogenosilane is consumed by the conversion into the diorganohalogenosilane and also by the distillation. In the reaction system, the compound formed by conversion of the ≡Si—H moiety of the organosilicon compound into an ≡Si—Y moiety increases in amount as time passes. As a result, the concentration of th diorganodihalogenosilane in the system decreases. This causes a relative concentration of the diorganohalogenosilane to the diorganodihalogenosilane to increase, thereby entailing the side reactions mentioned before. Accordingly, the diorganodihalogenosilane must be appropriately supplied during the reaction. The diorganodihalogenosilane should be supplied or added such that the system is controlled to contain the diorganodihalogenosilane in an amount of from 2 to 10 times by mole based on the ≡Si—H bond of the organosilicon compound. If the compound which has been formed by conversion of the ≡Si—H bond of the organosilicon compound into the less active ≡Si—Y bond is withdrawn from the system at a given rate, continuous operations will become possible.

The dropping rate of the starting material is not critical and is preferably in the range of from 0.1 to 20 moles/liter·hour from the standpoint of handling and productivity.

Since the reaction of the invention proceeds in the presence of a small amount of the catalyst, a very small amount may be sufficient. However, the moisture in the starting materials and the siloxanes will deactivate the catalyst, the amount of the catalyst is generally not less than 0.1 wt % of the total weight of the reaction system according to the invention. If deactivated, the catalyst may be added.

With the distilled mixture of the diorganohalogenosilane and diorganodihalogenosilane, the diorganohalogenosilane is subsequently separated by distillation. If the Lewis acid such as AlCl₃ is contained even in small amounts, the side reactions will take place during the distillation, with a lowering of the yield. In the worst case, the purification by the distillation will become impossible. Accordingly, the concentration of the Lewis acid in the distillate should be not larger than 50 ppm, preferably not larger than 10 ppm. To this end, when the mixture of the diorganohalogenosilane and diorganodihalogenosilane is distilled during the reaction, the distillation is performed while appropriately controlling a reflux ratio through a distillation column. If the side reactions take place by incorporation of the Lewis acid during the distillation, substances capable of deactivating the Lewis acid, e.g. siloxanes or amines as used in the first embodiment, may be added in small amounts by which the side reactions can be inhibited.

In the second embodiment, the final diorganohalogenosilane can be obtained at a yield of approximately 90% or over. Thus, a higher yield is expected than in the first embodiment.

As will be apparent from foregoing, the process of the invention enables one to selectively obtain diorganohalogenosilanes and particularly, dimethylmonochlorosilane, at low costs and at high yield.

The present invention is more particularly described by way of examples.

EXAMPLE 1

In this example, an apparatus shown in the sole FIGURE was used. In the FIGURE, a reactor 1 is placed on an oil bath 2 which is mounted on a magnetic stirrer. The reactor 1 contains a starting diorganodichlorosilane 4, such as dimethyldichlorosilane, dispersing a Lewis acid. Indicated at 5 is a rotator. The reactor 1 is equipped with dropping funnels 6, 7 for starting materials and also with a distillation column 9 which is connected to a distillate receptacle 8 through a condenser 10.

52.4 g of dimethyldichlorosilane and 10 g of aluminum chloride were charged into the reactor and heated while agitating under total reflux. Thereafter, 12.01 g/hour of tetramethyldisilane was dropped into the content. While dimethyldichlorosilane was added in such a way that the reactor temperature was maintained at 70° to 80° C. and the distillation was effected at a distillation temperature of 55° to 65° C., the reaction was continued for 1 hours. During the reaction, the amount of the distillate was 44.3 g. The content of the dimethylmonochlorosilane was 39.5% and the yield was 91.0%.

The resultant mixture was subjected to further distillation to obtain 13.1 g of a fraction having a boiling point of 34° to 36° C.

This fraction was analyzed by gas chromatography with a purity of 98% and the retention time being coincident with that of a reference compound. Moreover, the results of an EI-mass spectroscopy revealed that a standard peak m/e of 93 was ascribed to $[(CH_3)_2{}^{28}Si^{35}Cl]^+$ and a peak m/e of 89 ascribed to $[CH_3{}^{28}SiH^{35}Cl]^+$, which peaks coincided with those of a reference compound.

The NMR spectra were measured with the following results.

0.2 ppm (d, 6H):H—Si(CH$_3$)$_2$Cl;
3.7–4.2 ppm (m,1H):H—Si(CH$_3$)$_2$Cl.

These spectra were the same as those of the reference compound.

EXAMPLE 2

The general procedure of Example 1 was repeated except that the dropping rate of the tetramethyldisilane was changed to 36.03 g/hour, thereby obtaining 17.8 g of dimethylmonochlorosilane at a yield of 92.5%.

EXAMPLES 3 to 6

The general procedure of Example was repeated except that the tetramethyldisilane was substituted with different silanes indicated in Table below. As a result, it was found that dimethylmonochlorosilane could be obtained at high yields in all the examples.

TABLE

| Example | Starting Polysilane | Mixing Ratio | Yield (%) |
|---|---|---|---|
| 3 | bisdimethylsilylmethane | 100 | 90 |
| 4 | tetramethyldisilane | 70 | 92 |
|   | bisdimethylsilylmethane | 30 |   |
| 5 | hexamethyltrisilane | 100 | 89 |
| 6 | diemthylsilylmonomethylsilylmethane | 50 | 93 |
|   | tetramethyldisilane | 50 |   |

EXAMPLE 7

47.1 g of diethyldichlorosilane and 2 g of aluminum chloride were charged into a reactor, followed by dropping 8 g of tetramethyldisilane in one hour in the same manner as in Example 1 and further dropping diethyldichlorosilane while keeping the reactor temperature at 140° C. The distillation temperature during the reaction was from 125 to 130° C. and the amount of distillate was 55.2 g with a content of diethylchlorosilane of 28% and a yield of 15.4 g (93%).

What is claimed is:

1. A process for the preparation of a diorganohalogenosilane which comprises reacting a diorganodihalogenosilane and at least one organosilicon compound having at least one ≡Si—H bond in the molecule and selected from polysilanes, polycarbosilanes and polysilphenylenes in the presence of a Lewis acid.

2. The process according to claim 1, wherein said at least one organosilicon compound is of the general formula

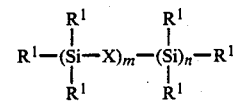

wherein each $R^1$ independently represents a hydrogen atom, a lower alkyl group having from 1 to 3 carbon atoms, an alkenyl group, or an aryl group provided that at least one $R^1$ is a hydrogen atom, X represents —(CH$_2$)$_l$— wherein l is an integer of from 1 to 3, or

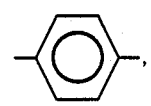

m is an integer of from 0 to 3 and n is an integer of from 1 to 5 provided that m+n≧2.

3. The process according to claim 1, wherein said at least one organosilicon compound is tetramethyldisilane.

4. The process according to claim 1, wherein said at least one organosilicon compound is bis(dimethylsilyl)methane.

5. The process according to claim 1, wherein said at least one organosilicon compound is diemthylsilylmonomethylsilylmethane.

6. The process according to claim 1, wherein said diorganodihalogenosilane is of the general formula

wherein each $R^2$ independently represents an alkyl group having from 1 to 10 carbon atoms, an alkenyl group or an aryl group and each Y independently represents chlorine, bromine or iodine.

7. The process according to claim 6, wherein said diorganodihalogenosilane is dimethyldichorosilane.

8. The process according to claim 1, wherein said Lewis acid is aluminum chloride.

9. The process according to claim 1, wherein the reaction is effected by adding said at least one organosilicon compound to a mixture of said diorganodihalogenosilane and the Lewis acid at a temperature ranging from room temperature to the refluxing temperature of the diorganodihalogenosilane and adding a terminator for the reaction when a desired yield of the diorganohalogenosilane is attained.

10. The process according to claim 9, wherein the diorganohalogenosilane is separated from the mixture.

11. The process according to claim 1, wherein the reaction is effected by adding said at least one organosilicon compound into a mixture of said diorganodihalogenosilane and the Lewis acid in a reaction system while removing the resultant diorganohalogenosilane from the mixture.

12. The process according to claim 11, wherein the removal of the diorganohalogenosilane is carried out by subjecting the mixture to distillation at a temperature higher than the boiling point of the diorganohalogenosilane.

13. The process according to claim 12, wherein the resultant distillate has a content of the diorganohalogenosilane of not higher than 70 mole %.

14. The process according to claim 12, wherein the distillation is effected such that the content of Lewis acid in the distillate is not larger than 50 ppm.

15. The process according to claim 11, wherein during the reaction, the diorganodihalogenosilane is added such that the reaction system is controlled to contain the diorganodihalogenosilane in an amount of from 2 to 10 times by mole based on the ≡Si—H bond of the at least one organosilicon compound.

16. The process according to claim 1, wherein when the ≡Si—H bond of the at least one organosilicon compound is converted into a less active bond by the reaction, the converted organosilicon compound is continuously removed from a system of the reaction whereby the reaction is carried out continuously.

17. The process according to claim 1, wherein the Lewis acid is used in an amount of not less than 0.1 wt % based on the total weight of a system of the reaction.

* * * * *